United States Patent
Nittinger

[11] Patent Number: 5,778,480
[45] Date of Patent: Jul. 14, 1998

[54] DENTAL HYGIENIST'S DEVICE

[76] Inventor: Susan R. Nittinger, 122 S. Concord Ter., Absecon, N.J. 08201

[21] Appl. No.: 731,207

[22] Filed: Oct. 10, 1996

Related U.S. Application Data

[60] Provisional application No. 60/004,930 Oct. 10, 1995.

[51] Int. Cl.$^6$ .............................. A47L 25/00; A61C 19/00
[52] U.S. Cl. .................... 15/210.1; 15/218.1; 15/220.4; 15/244.1; 15/244.3
[58] Field of Search ................ 15/104.92, 210.1, 15/211, 218, 218.1, 220.4, 244.1, 221, 244.3, 423

[56] References Cited

U.S. PATENT DOCUMENTS

| 189,081 | 4/1877 | Cassel et al. | 15/218.1 |
| 958,843 | 5/1910 | Uhlyarik | 15/218.1 |
| 2,425,469 | 8/1947 | Hanrahan et al. | 451/65 |
| 2,556,003 | 6/1951 | Sandell et al. | 15/104.92 |
| 3,765,047 | 10/1973 | Tashjian | 15/118 |
| 4,011,693 | 3/1977 | Eldridge, Jr. et al. | 451/486 |
| 4,506,404 | 3/1985 | Clay | 15/244.3 |
| 4,752,983 | 6/1988 | Grieshaber | 15/160 |
| 5,016,401 | 5/1991 | Mangus | 451/59 |

FOREIGN PATENT DOCUMENTS

| 36164 | 7/1886 | Germany | 15/218.1 |
| 62928 | 7/1892 | Germany . | |
| 10215 | 5/1892 | United Kingdom . | |
| 26945 | 11/1906 | United Kingdom | 15/218.1 |
| 167364 | 3/1921 | United Kingdom . | |
| 443523 | 3/1936 | United Kingdom . | |

*Primary Examiner*—Mark Spisich
*Attorney, Agent, or Firm*—Norman E. Lehrer

[57] ABSTRACT

A dental hygienist's device for removing debris from dental tools wherein a cleaning head is disposed atop a saucer member such that debris is wiped onto the cleaning head and fallen debris collects in the saucer member. The device is adapted to be attached to various surfaces in a dental operatory via a vise clamp. If no surface for attachment is available, the device may be combined with a conventional dental operatory standing tray.

12 Claims, 4 Drawing Sheets

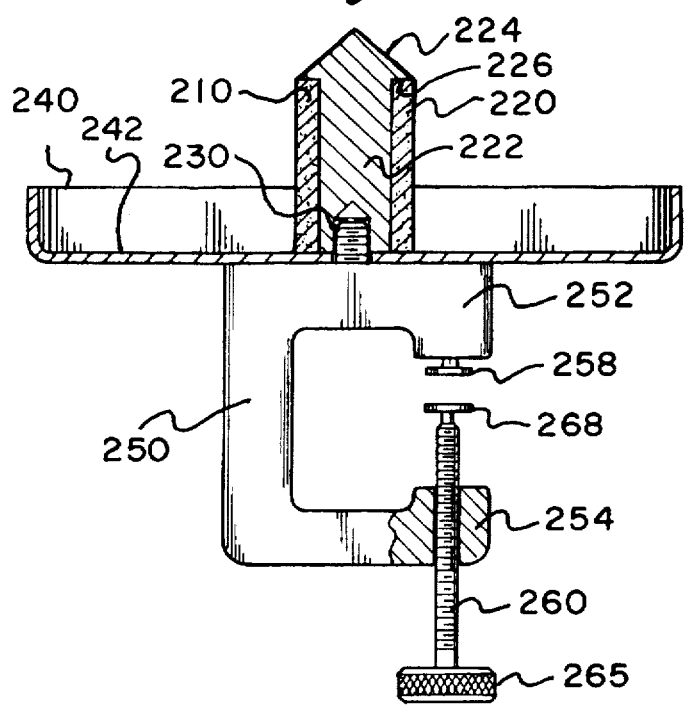
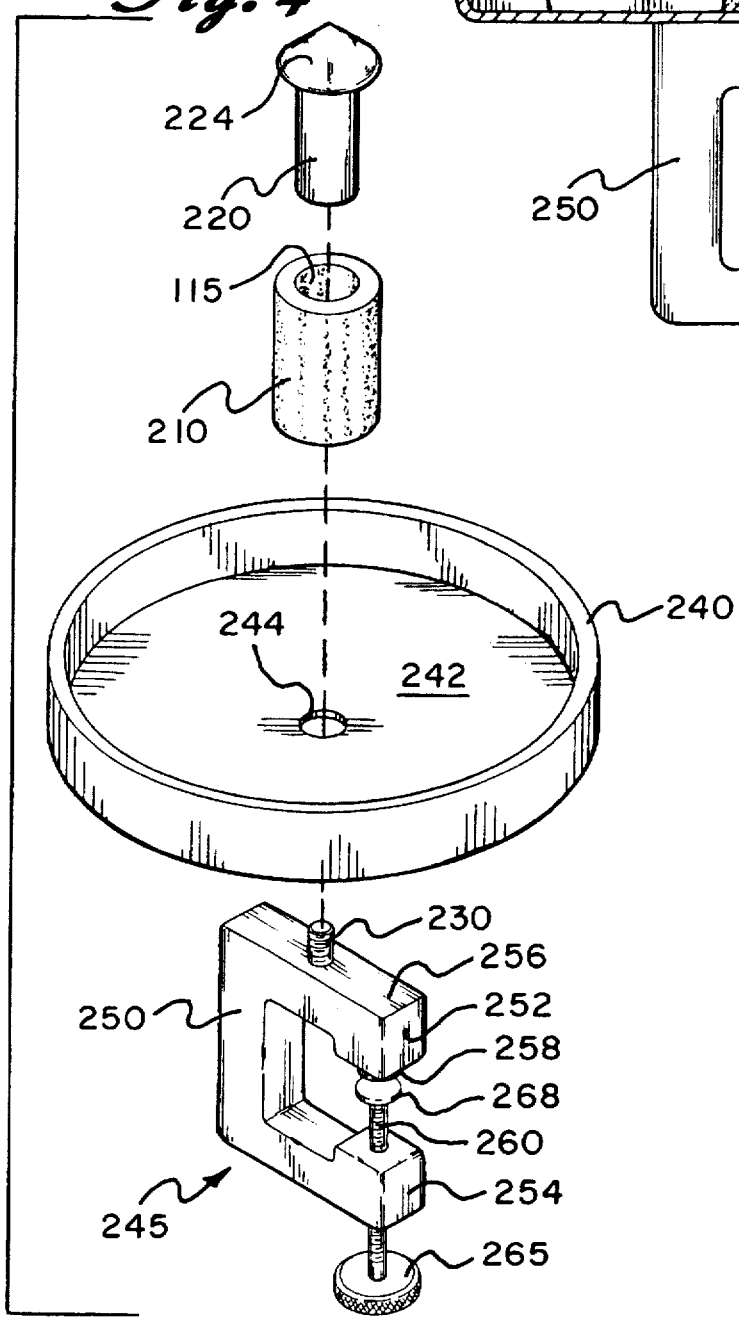

DENTAL HYGIENIST'S DEVICE

CROSS-REFERENCE TO RELATED APPLICATION

This application claims the benefit of U.S. provisional patent application Ser. No. 60/004,930, filed Oct. 10, 1995.

FIELD OF THE INVENTION

The present invention relates to an apparatus for cleansing dental instruments and capturing debris therefrom. The apparatus includes a cleaning head, a cleaning head support, and a saucer for catching debris. The shape of the cleaning head allows a variety of dental hygiene tools to communicate with it, while the saucer is configured to conveniently fix the head and serve as a receptacle.

DESCRIPTION OF PRIOR ART

The prior art illustrates a variety of devices adapted to facilitate cleansing. Typically, many of the prior art type cleansing devices have adaptations for capturing debris. Additionally, they are often specifically shaped to effectively interact with other cleansing devices.

U.S. Pat. No. 189,081, issued Apr. 3, 1877, to D. H. Cassel and G. W. Zint discloses a knife-scouring pan having a dish with a vertically inclined rest piece. Unlike the present invention, Cassel and Zint's device does not provide an elevated member for capturing debris. Further, Cassel and Zint's device does not allow for quick cleaning.

U.S. Pat. No. 958,843, issued May 24, 1910, to Anthony Uhlyarik discloses a machine for use in cleaning table cutlery. Uhlyarik's device has pads on which an abrasive substance may be applied and between which knives and forks may be tightly squeezed. Unlike the present invention, Uhlyarik's device does not possess an elevated tip for receiving debris. Also, no sauce type receptacle is provided to catch falling debris.

U.S. Pat. No. 2,425,469, issued Aug. 12, 1947, to E. M. Hanrahan et al. discloses a polishing machine for tableware including a motor, a disc, and a polishing cloth. Hanrahan's device is provided with an oval burnishing unit, however, the burnishing unit must be fixedly attached to a motor. Additionally, unlike the present invention, Hanrahan's device does not have a receptacle for capturing debris.

U.S. Pat. No. 2,556,003, issued Jun. 5, 1951, to George E. Sandell and Beatrice E. Sandell discloses a water glass and a cup washer comprising a cylindrical sponge mounted on a suction cup. Unlike the present invention, Sandell and Sandell's device does not have a receptacle for catching debris.

U.S. Pat. No. 3,765,047, issued Oct. 16, 1973, to Artin Tashjian discloses a combined soldering gun support and tip cleaner. Unlike the present invention, Tashjian's device does not have a receptacle for catching debris.

U.S. Pat. No. 4,011,693, issued Mar. 15, 1977, to John D. Eldridge, Jr. et al. discloses a cleaner for cauterizing instruments wherein vertically disposed magnet elements with abrasive material provide a surface on which instruments may be wiped. Unlike the present invention, Eldridge's device does not disclose an elevated tip on which debris is captured, nor does it provide a saucer for collection of debris.

U.S. Pat. No. 4,506,404, issued Mar. 26, 1985, to Ambrose W. J. Clay discloses a disposable sponge having a rectangular base member with rectangular members disposed perpendicular to the plane of the base member.

U.S. Pat. No. 4,752,983, issued Jun. 28, 1988, to Herman R. Grieshaber discloses a surgical instrument cleaning device having a hollow casing with a slot for insertion of surgical instruments.

U.S. Pat. No. 5,016,401, issued May 21, 1991, to Donald J. Mangus discloses a cautery tip cleaner and holder having a circular pad mounted to a rectangular base. Unlike the present invention, Mangus' invention does not have a saucer for collecting debris. Also, Mangus' invention does not have a debris-capturing tip elevated on an elongated member.

German Patent No. 62928, issued Jul. 1, 1892, to Alfred Graser discloses a pen cleaner having a container for cleansing fountain pens. A user inserts a pen tip into the container such that an annular brush disposed within the container removes any dry ink from the pen tip. Unlike the present invention, Graser's invention does not have an elevated tip for capturing debris Also Graser's invention does not employ a saucer to catch debris which might fall from an elevated tip.

British Patent No. 10,215, issued Apr. 1, 1893, to Friedrich Heinrich Eversmarin discloses a knife-cleaning device wherein a blade is passed to and fro between two rubbing strips of leather. Unlike the present invention, no means is provided for quick and readily disposable removal of debris from a dental hygiene tool. Additionally, no means is employed for capturing debris which might fall after removal.

British Patent No. 167,364, issued Aug. 11, 1921, to William Cook discloses a blade/knife cleaning and polishing device having a sheet of felt disposed between two metal plates wherein a knife or blade is placed on the felt. The metal plates are hinged together so that they may be brought together to exert pressure on the felt in order to clean and polish a knife or blade. Unlike the present invention, Cook's device does not employ a saucer to catch debris. Furthermore, Cook's device does not have an elevated tip for capturing debris.

British Patent No. 443,523, issued March 1936, to Swales discloses an oven cleaning device suitable for applying a liquid cleaning preparation to a surface to be cleaned. Swales' invention is similar in shape to a sword, and a user would use it by probing into the mouth of an oven. Unlike the present invention, Swales' invention does not have a saucer receptacle, does not have a removable head, and is not suitable for capturing debris from dental hygiene tools.

None of the above inventions and patents, taken either alone or in combination, is seen to describe the instant invention as claimed.

SUMMARY OF THE INVENTION

Accordingly, it is a principal object of the invention to provide a dental hygienist's device which is fully capable of removing debris from dental hygiene tools.

It is another object of the invention to provide a dental hygienist's device which is readily adaptable to conventional dental hygiene work station.

It is a further object of the invention to provide a dental hygienist's device having means for quickly and easily disposing of collected debris.

Still another object of the invention is to provide a dental hygienist's device which remains stationary as variously sized tools are rubbed against it.

It is an object of the invention to provide improved elements and arrangements thereof in an apparatus for the purposes described which is inexpensive, dependable and fully effective in accomplishing its intended purposes.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

FIG. 4 is an exploded perspective view of a second embodiment of the present invention, and FIG. 5 is a vertical partial cross-sectional view of the second embodiment of FIG. 4.

DETAILED DESCRIPTION OF THE PREFERRED EMBODIMENTS

Figure 1:
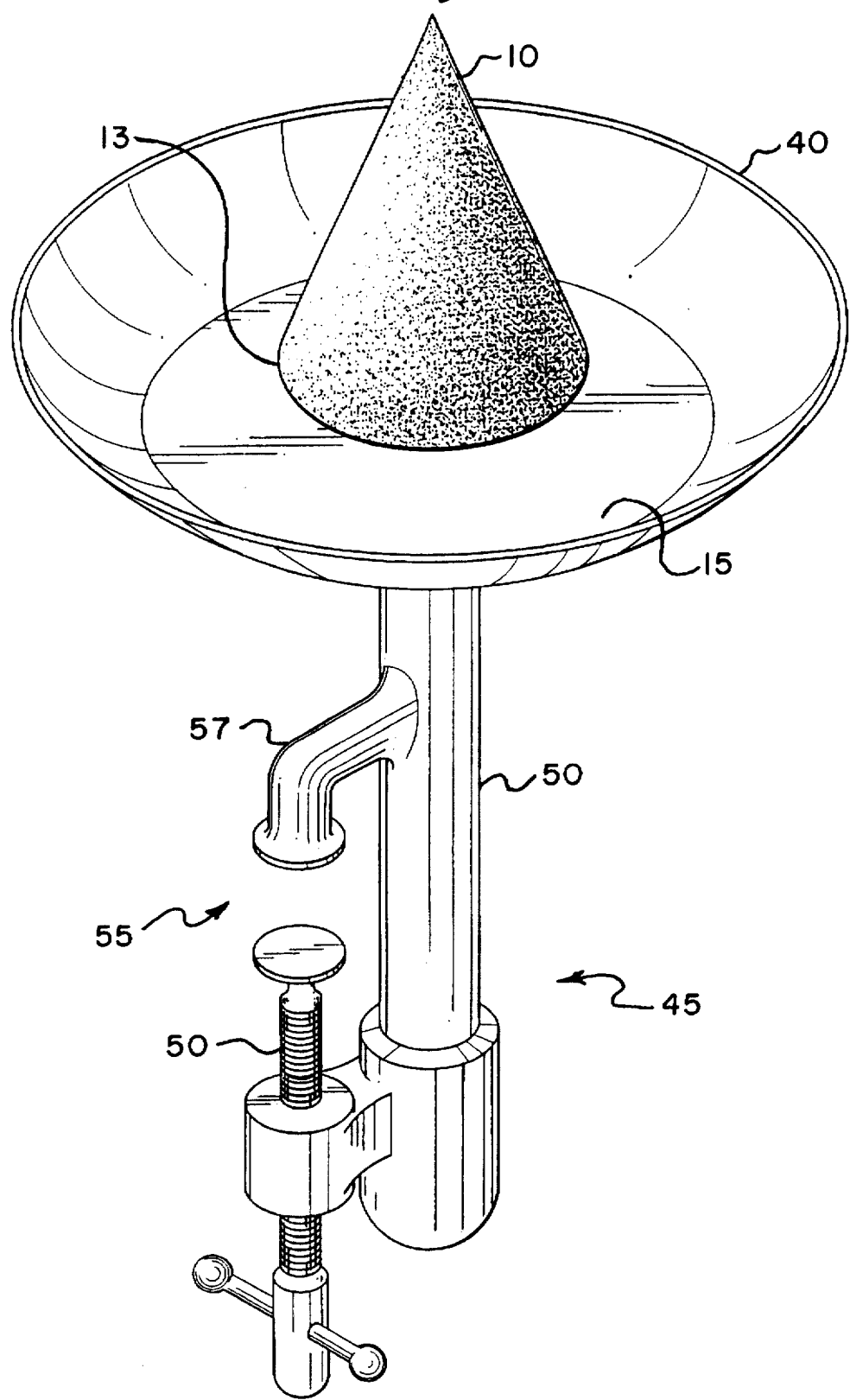
FIG. 1 is a front perspective view of a first embodiment of the present invention.

Referring now to the drawings in detail wherein like numerals have been used throughout the various figures to designate like elements, a first embodiment of the present invention is shown in FIG. 1 to have a conical head 10 disposed within and above a saucer member 40. The conical head 10 is preferably mounted centrally on saucer upper surface 15 such that conical head base 13 communicates with saucer upper surface 15. The conical head 10 may be entirely made of gauze, or alternatively, it may be made of a resilient material on which gauze can be wrapped around. The saucer member 40 is preferably made of stainless steel or other material which can be easily washed and wiped clean between uses.

A conventional clamp 45 provides the present invention with a means of attachment to any sturdy, non-moving object (not shown) located in an operatory (not shown). The conventional clamp 45 comprises a stabilizing member 50 which is preferably disposed centrally and below the saucer member 40 such that the saucer member 40 is fully supported and balanced.

The conventional clamp 45 also comprises a vise section 55. Two components of the vice section 55, arm member 57 and screw member 60, are disposed so that the clamp 45 can be fixedly attached to a surface perpendicular to the plane of the stabilizing member 50. A user can turn screw member 60 such that the distance between screw member 60 and arm member 57 increases or decreases as necessary to apply pressure to a surface perpendicular to the plane of the stabilizing member 50.

Figure 3:
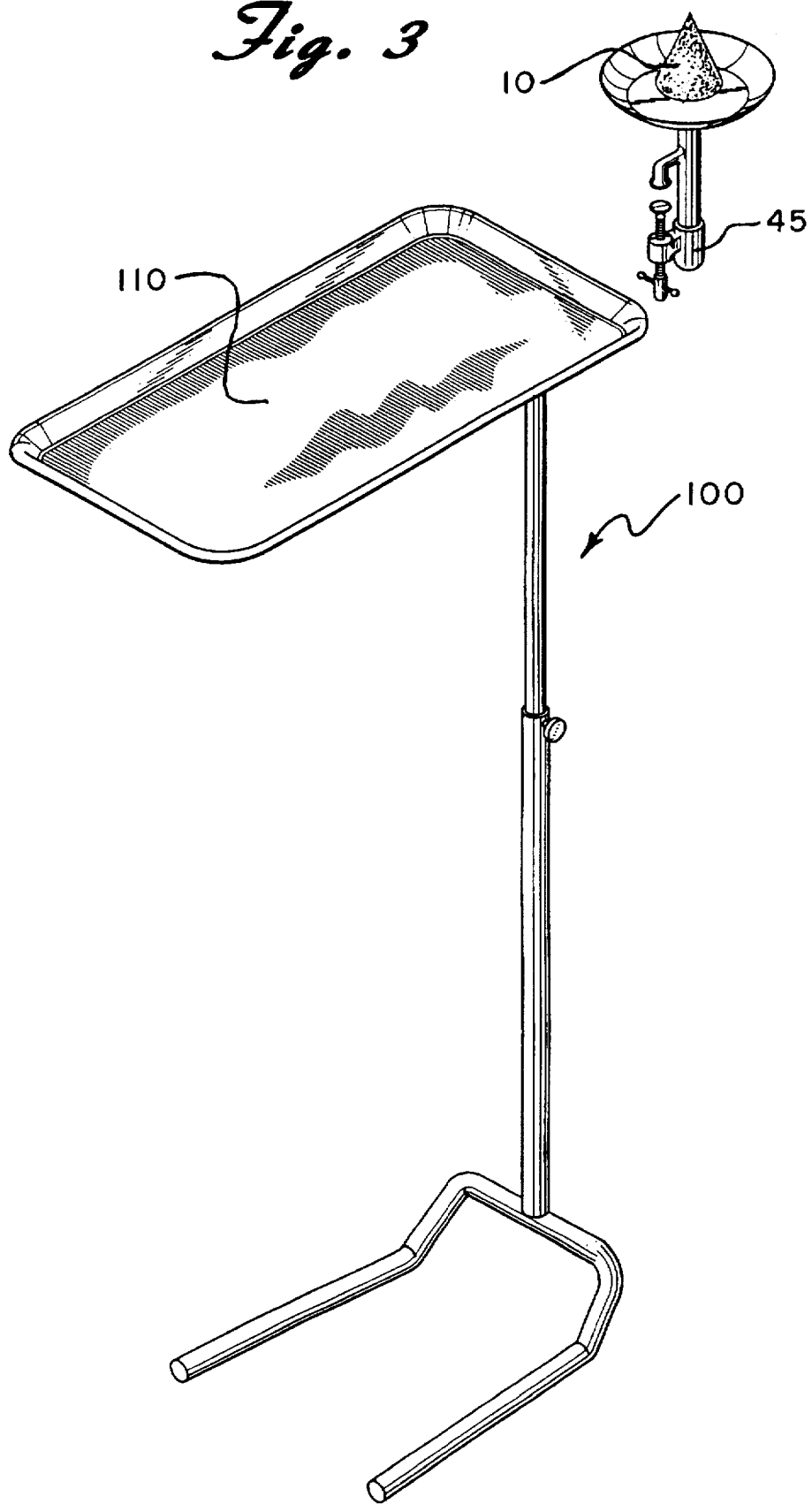
FIG. 3 is an environmental partially exploded, perspective view of the first embodiment of the invention ready for attachment to a stand.

In FIG. 3, the present invention is shown to include a conventional operatory standing tray 100. If an operatory does not have a surface suitable for attachment of clamp 45, conventional operatory standing tray 100 is provided with tray piece 110. Clamp 45 can be fixedly attached to tray piece 110 such that the present invention is readily accessible for use.

Figure 2:
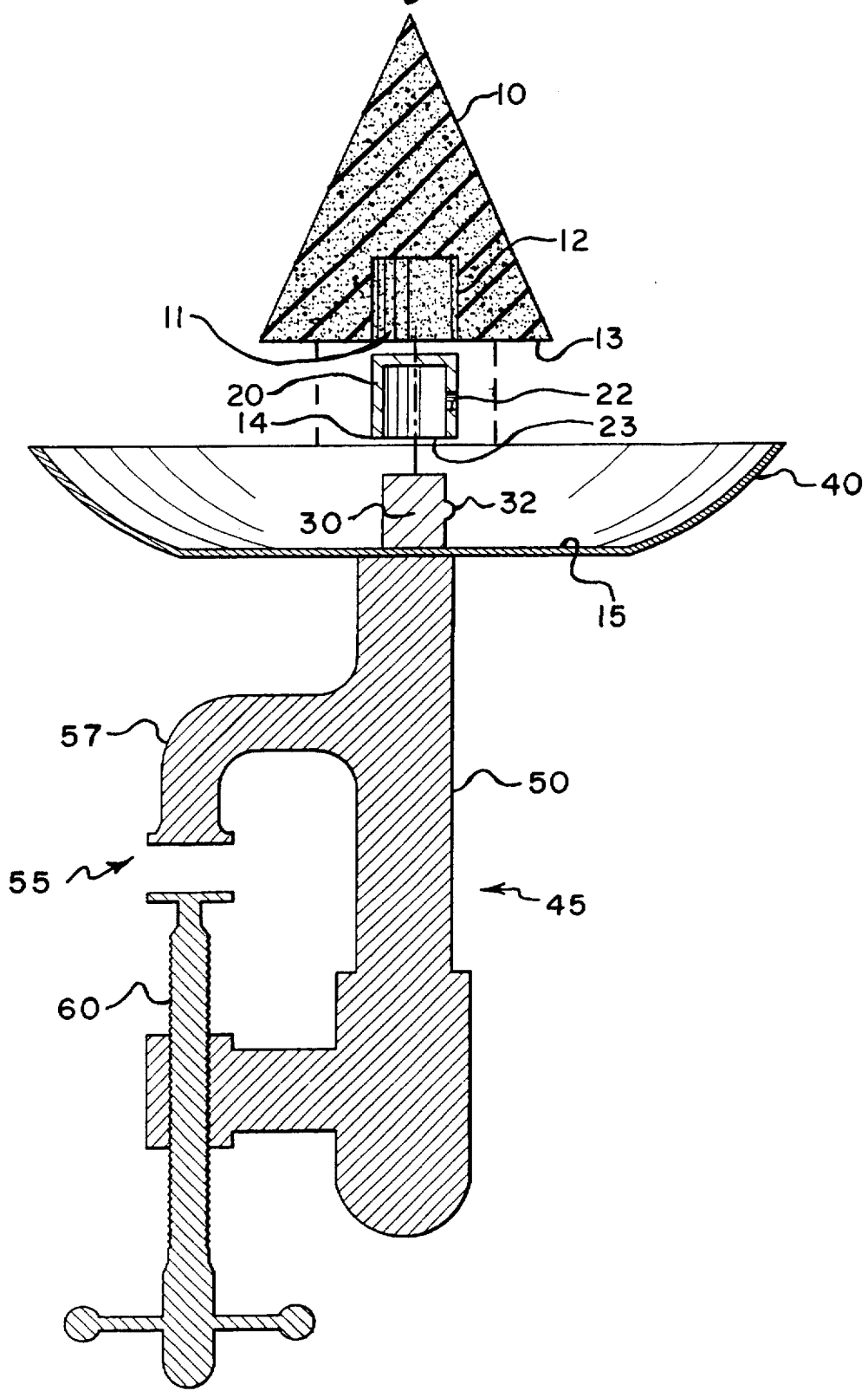
FIG. 2 is a right side, partially exploded, sectional view of the embodiment shown in FIG. 1.

Referring to FIG. 2, the present invention is shown disassembled in order to illustrate the method by which the conical head 10 is attached to the saucer member 40. Conical head 10 is shown above and unattached to saucer member 40. Conical head base 13 has a hollow cubical region II positioned centrally at the bottom of conical head 10 such that conical head 10 is substantially solid except for hollow cubical region 11.

Hollow cubical region 11 is dimensioned to receive adapter piece 20 so as to fixedly fit onto neck 30. Adapter piece 20 is a substantially hollow cube with an orifice 22 and an open bottom 23. Orifice 22 is centrally disposed on the side of adapter piece 20. Hollow cubical region 11 is dimensioned to have a slightly greater height, length and width than adapter piece 20 such that when adapter piece 20 is placed inside hollow cubical region 11, conical head base 13 meets adapter piece base 14 in the same plane. Neck 30 is cubical in shape and has a nub 32 extending from one of its sides. Neck 30 is also dimensioned to have a slightly lesser height, length and width than adapter piece 20.

A user assembles the present invention by placing adapter piece 20 on neck 30 such that nub 32 is exposed through orifice 22. Conical head 10 is placed on adapter piece 20 such that nub 32 communicates with the hollow cubical region side 12. In the embodiment shown, hollow cubical region side 12 is relatively flat. Resilient but flexible conical head 10 flexes to allow nub 32 to press into hollow cubical region side 12. The pressure of nub 32 against hollow cubical region side 12 holds conical head 10 atop adaptor piece 20. There is preferably no orifice in hollow cubical region 11 to receive nub 32. However, a bore (not shown) could be formed in hollow cubical region side 12 for receiving nub 32 to serve as a ball-and-socket type connection. In final assembled form, the conical head 10 is mounted centrally on saucer upper surface 15 such that conical head base 13 communicates with saucer upper surface 15.

The present invention is configured so that a user can wipe debris (not shown) from a dental hygienist's tool (not shown) into conical head 10. As the debris (not shown) is captured on conical head 10, it falls down into saucer member 40. After utilizing the present invention, the user can remove conical head 10 and either replace it or clean it. In addition, the user can clean the collected debris (not shown) from the saucer member 40.

A second embodiment of the invention is shown in FIGS. 4 and 5. Many of the component parts of the second embodiment are variations of similar component parts illustrated in the first embodiment described above. Accordingly, and for ease of understanding, wherever possible similar reference numerals have been utilized to designate similar elements. However, in the second embodiment, all reference numerals are preceded with the number 2. Thus, for example, the saucer member 40 of the embodiment shown in FIG. 1 is identified by the number 240 in the second embodiment shown in FIGS. 4 and 5.

In lieu of a conical head 10, the second embodiment utilizes a cylindrical member 210. The cylindrical member 210 is preferably comprised of synthetic foam which may be approximately 3 inches high. It is preferably in the form of a cylinder having an open center 215. The foam cylindrical member 210 is fitted onto an essentially mushroom-shaped adaptor piece 220 which has a cylindrically shaped lower portion 222 and a conical top 224. The top 224 is slightly larger than the cylindrical member 222. Accordingly, a peripheral flange 226 is created at the bottom of the conical top 224.

The diameter of the cylindrically shaped lower portion 222 is substantially the same as the inner diameter of the opening 215 in the foam member 210 so that the latter snugly but easily fits over the former. The length of the foam member 210 is slightly greater than the length of the cylindrically shaped lower member 222 so that the foam is slightly compressed when it is assembled in place.

The second embodiment shown in FIGS. 4 and 5 also includes a clamp member 245 of substantially C-shape having a vertical member 250 and upper and lower arms 252 and 254, respectively. A screw 260 is threaded through the forward portion of the lower arm 254 and can be turned utilizing the knurled knob 265. A gripping element 268 is located at the upper end of the screw 260 and a similar gripping element 258 extends downwardly from the forward end of the upper arm 252 so as to cooperate with each other in the known manner. Preferably, the gripping elements 258 and 268 may have a rubber coating or the like so as to protect the dental tray or other piece of equipment to which the device is attached.

The upper surface 256 of the upper arm 252 is substantially planar. Extending upwardly from substantially the center of the surface 256 is a threaded stud 230. The threaded stud 230 is intended to extend through the opening 244 in the bottom wall 242 of the saucer member 240. As best seen in FIG. 5, the lower surface of the adaptor piece 220 includes a threaded bore therein so that the adaptor piece 220 can be threaded onto the stud 230 (after a foam element 210 is placed on the adaptor piece 220) so that all of the elements can be secured together in the manner illustrated.

With the exception of the foam element 210, the majority of the major components of the invention shown in the second embodiment are preferably comprised of aluminum. The device is, therefore, relatively light but can be easily cleaned when necessary. Furthermore, if desired, disposable paper or the like could be placed on the upper surface 242 of the saucer member 240.

In the second embodiment of the invention shown in FIGS. 4 and 5, the preferred shape of the foam cleaning head 210 is cylindrical. However, it is not beyond the scope of the present invention to utilize different shaped heads. Obviously, the shape of the adaptor piece 220 may have to change somewhat to accommodate other shapes of cleaning heads. It is intended, however, that the component parts will be assembled and will cooperate with each other in substantially the same manner as illustrated in FIGS. 4 and 5. Furthermore, it should be readily apparent that the second embodiment of the invention just described is utilized in substantially the same manner as the first embodiment described above. Accordingly, a detailed description of the manner in which the second embodiment is utilized is not believed to be necessary.

The present invention may be embodied in other specific forms without departing from the spirit or essential attributes thereof and accordingly reference should be made to the appended claims rather than to the foregoing specification as indicating the scope of the invention.

I claim:

1. A dental hygienist's device for removing debris from dental hygiene tools, comprising:

a saucer member for collecting debris, said saucer member having a bottom wall;

a conically shaped cleaning head for capturing debris when a dental hygienist's tool is wiped thereon, said cleaning head being mounted on said saucer member substantially centrally of said bottom wall, and extending upwardly therefrom, and a clamp means beneath said saucer member for attaching said saucer member and said cleaning head to a surface located in a conventional dental operatory.

2. The dental hygienist's device according to claim 1, wherein said cleaning head is comprised of a resilient material.

3. The dental hygienist's device according to claim 2, wherein said cleaning head further includes an adapter means for supporting said resilient material.

4. The dental hygienist's device according to claim 3, further including screw means for securing said adapter means to said saucer member and to said clamp means.

5. The dental hygienist's device according to claim 4, wherein said screw means is mounted on said clamp means and extends through an opening in said saucer member.

6. The dental hygienist's device according to claim 3, wherein said adapter means includes a cylindrical portion and an enlarged portion mounted on top of said cylindrical portion.

7. The dental hygienist's device according to claim 6, wherein said cleaning head includes a resilient member that fits over said cylindrical portion.

8. A dental hygienist's device for removing debris from dental hygiene tools, comprising:

a saucer member for collecting debris, said saucer member having a bottom wall;

a cleaning head for capturing debris when a dental hygienist's tool is wiped thereon, said cleaning head being mounted on said saucer member substantially centrally of said bottom wall, and extending upwardly therefrom;

said cleaning head being comprised of a resilient material and including an adapter means for supporting said resilient material;

clamp means beneath said saucer member for attaching said saucer member and said cleaning head to a surface located in a conventional dental operatory, and screw means for securing said adapter means to said saucer member and to said clamp means.

9. The dental hygienist's device according to claim 8, wherein said cleaning head is cylindrically shaped.

10. The dental hygienist's device according to claim 8, wherein said screw means is mounted on said clamp means and extends through an opening in said saucer member.

11. The dental hygienist's device according to claim 8, wherein said adapter means includes a cylindrical portion and an enlarged portion mounted on top of said cylindrical portion.

12. The dental hygienist's device according to claim 11, wherein said cleaning head includes a resilient member that fits over said cylindrical portion.

* * * * *